US008436251B2

(12) United States Patent
Boyd

(10) Patent No.: US 8,436,251 B2
(45) Date of Patent: May 7, 2013

(54) RIBBON CONNECTING ELECTRICAL COMPONENTS

(75) Inventor: Steven Boyd, Litchfield Park, AZ (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 12/499,319

(22) Filed: Jul. 8, 2009

(65) Prior Publication Data

US 2011/0005813 A1 Jan. 13, 2011

(51) Int. Cl.
 *H05K 1/09* (2006.01)
 *H05K 7/00* (2006.01)
 *H01R 9/00* (2006.01)
 *H01L 29/40* (2006.01)

(52) U.S. Cl.
 USPC ........... 174/257; 361/776; 361/777; 361/779; 257/784

(58) Field of Classification Search .................... 174/257
 See application file for complete search history.

(56) References Cited

U.S. PATENT DOCUMENTS

| 3,494,028 | A |   | 2/1970  | Flanders et al. |             |
|-----------|---|---|---------|-----------------|-------------|
| 3,734,386 | A | * | 5/1973  | Hazel           | 228/4.5     |
| 3,965,277 | A | * | 6/1976  | Guditz et al.   | 430/319     |
| 5,235,212 | A | * | 8/1993  | Shimizu et al.  | 257/780     |
| 5,358,796 | A | * | 10/1994 | Nakamura et al. | 428/660     |
| 5,367,195 | A | * | 11/1994 | DiGiacomo et al.| 257/767     |
| 6,032,850 | A | * | 3/2000  | Orcutt          | 228/4.5     |
| 6,184,587 | B1| * | 2/2001  | Khandros et al. | 257/784     |
| 6,296,493 | B1| * | 10/2001 | Michiya         | 439/66      |
| 6,384,486 | B2| * | 5/2002  | Zuniga et al.   | 257/781     |
| 6,428,634 | B1| * | 8/2002  | Besselink et al.| 148/421     |
| 6,767,440 | B1| * | 7/2004  | Bhullar et al.  | 204/403.01  |
| 6,858,943 | B1| * | 2/2005  | Peterson et al. | 257/784     |
| 7,015,580 | B2| * | 3/2006  | Fitzsimmons et al.| 257/739   |
| 7,214,068 | B2| * | 5/2007  | Kronich et al.  | 439/65      |
| 7,319,277 | B2| * | 1/2008  | Lin             | 257/781     |
| 7,385,297 | B1| * | 6/2008  | Gumaste et al.  | 257/784     |
| 7,397,125 | B2| * | 7/2008  | Oda             | 257/758     |
| 8,004,092 | B2| * | 8/2011  | Lin et al.      | 257/781     |
| 8,022,558 | B2| * | 9/2011  | Law et al.      | 257/781     |

(Continued)

FOREIGN PATENT DOCUMENTS

| EP | 2051304    | A1 | * | 4/2009  |
| JP | 62291153   | A  | * | 12/1987 |
| JP | 2000022309 | A  | * | 1/2000  |

OTHER PUBLICATIONS (PCT/US2010/041299) PCT Notification of Transmittal of the International Search Report and the Written Opinion of the International Searching Authority, Oct. 14, 2010.

*Primary Examiner* — Timothy Thompson
*Assistant Examiner* — Nathan Milakovich
(74) *Attorney, Agent, or Firm* — Carol F. Barry

(57) ABSTRACT

Articles and methods of manufacture are provided for using laser energy in an automated bonding machine to effect laser welding of ribbons to electronic components, particularly conductive ribbons comprising titanium for microelectronic circuits. Bonding and connection of microelectronic circuits with discrete heating avoids heat damage to peripheral microelectronic components. Bonding of flexible materials and low-resistance materials are possible, and are less dependant on substrate and terminal stability in comparison to other bonding methods. The ribbon-connections can forgo the use of blocks, bond pads, and bond pad arrays for attaching ribbon to a printed wiring board. Profile height of the ribbon-connection is decreased and the density of ribbons and bonding sites can be increased compared to ribbon-connections employing bonding pads.

21 Claims, 1 Drawing Sheet

U.S. PATENT DOCUMENTS

| | | |
|---|---|---|
| 2002/0045921 A1 | 4/2002 | Wolinsky et al. |
| 2003/0042621 A1* | 3/2003 | Chen et al. ............... 257/784 |
| 2004/0070042 A1* | 4/2004 | Lee et al. ............... 257/459 |
| 2005/0007718 A1* | 1/2005 | Stevenson et al. ............ 361/118 |
| 2005/0098605 A1* | 5/2005 | Edelstein et al. ............ 228/4.5 |
| 2006/0055023 A1* | 3/2006 | Ho et al. ............... 257/692 |
| 2007/0096313 A1* | 5/2007 | Chou et al. ............... 257/737 |
| 2007/0151351 A1 | 7/2007 | Schugt |
| 2007/0167989 A1 | 7/2007 | Sleeper |
| 2007/0182364 A1* | 8/2007 | Zhao et al. ............... 320/107 |
| 2008/0054420 A1* | 3/2008 | Quah et al. ............... 257/676 |

* cited by examiner

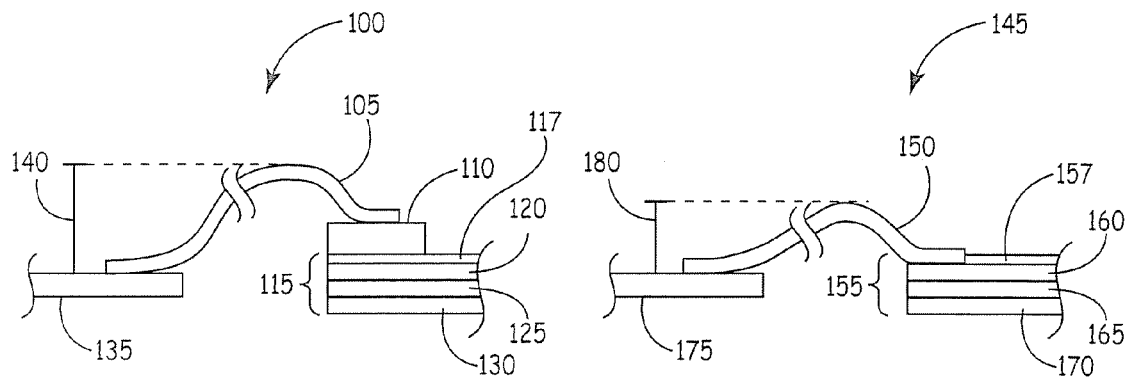
FIG. 1A (PRIOR ART)
FIG. 1B
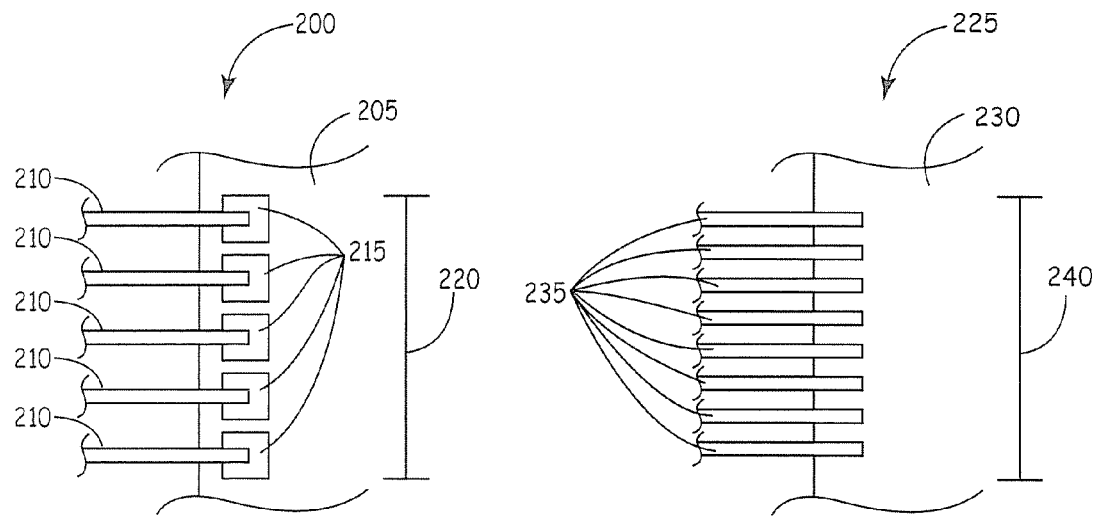
FIG. 2A (PRIOR ART)
FIG. 2B

RIBBON CONNECTING ELECTRICAL COMPONENTS

INTRODUCTION

The present technology relates to methods and articles of manufacture for joining conductive members, including conductive coupling of electronic and microelectronic circuits using a ribbon bond.

Electronic circuits, such as microelectronic logic circuits, or other similar electronic circuits, may be fabricated as an integrated unit, which has developed into a highly efficient method of compact circuit manufacture. Ultimately, however, the integrated circuit components or other packaged electronics typically are connected to larger circuits in order to be utilized, and be interconnected via lead frames or other connectors with circuits such as input and display apparatus, power supplies and grounds, and complementary circuits. Given the size of such circuits, the connection of these circuits takes place on a relatively small scale. For example, integrated circuit chips typically can be less than 0.3 inches×0.3 inches. These circuits may be interconnected by very small wires, e.g. wires with about one mil diameter, or by small, flat conductive metal ribbons which may be, for example, about 1×10 mils (0.001 inches×0.01 inches).

Various ribbon bonders and specialized solid-state bonding methods can be used to bond ribbon wires to substrates, lead frames, or various electronic components. For example, ultrasonic energy, a high-frequency vibration, e.g. from 60 KHz to over 100 KHz, can be imparted to the bond location by a bond head. Resistance welding is another bonding method used to heat metal and create a molten pool that will harden into a welding nugget. Laser-generated heat has also found application in certain part-joining methods. For example, lead frames have been soldered with lasers in applications such as tape automated bonding (TAB), utilized, for example, in U.S. Pat. No. 4,893,742 to Bullock. Bonding machines employing these various techniques and methods may use optics and pattern-matching logic systems in order to automate the bonding process for a particular package, device, or circuit being assembled.

Bond pads are used to provide a printed wiring board (PWB) or integrated circuit (IC) chip with one or more locations for bonding wires, ribbons, or other connectors; e.g., gold or aluminum wire. A bond pad can provide resistance to compressive forces, heat, and corrosion at the bonding site to protect the PWB and the electrical connection, and can provide metallurgical compatibility for welding or attachment of various metal wires or ribbons. When a PWB is fabricated, the yield is significantly affected by the potential number of bond pad locations and the reliability of the bond pads themselves. For example, chip size dictates the number of individual bond pads that may be attached thereto and inclusion of bond pads adds additional fabrication complexity. In some cases, a bond pad array (BPA) may be used to simplify manufacture and may also help increase the density of potential connections. Bond pads and bond pad arrays, however, can suffer from certain defects and/or damage and can also limit available spatial configurations. For example, a bond pad on a PWB can be damaged during the wire or ribbon bonding process or may suffer damage during subsequent probe testing procedures. The wire or ribbon bonding process also normally entails bonding of a metal wire or ribbon to the bond pad by fusing the bond pad and wire together using compressive force and/or thermal energy, which may consequently damage the bond pad. Damaged bond pads on a device can cause a part of a device to be discarded.

As PWBs have become smaller, feature sizes such as interconnect wire widths and spacing have been reduced and input/output (I/O) pin density has increased in order to increase productivity, but bond pads have generally not decreased in size or pitch (the center to center spacing of adjacent wire bond pads) proportionally to the decrease in chip and feature sizes. The industry has turned to other I/O pad types, such as solder bump, that offer greater I/O density, though at a greater cost which reduces productivity. Hence, there is a need to overcome the density and/or reliability limitations imposed by bond pads and bond pad arrays so that a cost-effective implantable device is delivered to a patient.

SUMMARY

The present technology includes systems, methods of manufacture, and articles of manufacture that relate to ribbon-connections. A ribbon-connection comprises a printed wiring board including a first bonding site, an electrical component including a second bonding site, and a ribbon comprising titanium. The ribbon includes a first end welded to the first bonding site of the printed wiring board and a second end welded to the second bonding site of the electrical component. The weld at the first bonding site directly contacts the printed wiring board and there is no bond pad provided between the ribbon and the first bonding site. The weld at the second bonding site may directly contact the electrical component where no bond pad is used between the ribbon and the second bonding site. The printed wiring board may further comprise a first electrically conductive layer and the first end of the ribbon welded to the first bonding site may directly contact the first electrically conductive layer. The first electrically conductive layer may comprise nickel or niobium.

In some embodiments, the ribbon-connection includes a printed wiring board that further comprises a second electrically conductive layer, wherein at least a portion of the second electrically conductive layer is located along the first electrically conductive layer opposite of the first bond site. In some embodiments, the weld at the first bond site does not affect the second electrically conductive layer. The portion of the second electrically conductive layer located along the first electrically conductive layer opposite of the first bond site may be substantially similar to another portion of the second electrically conductive layer not opposite of the first bond site. The second electrically conductive layer may comprise copper and the printed wiring board may further comprise a woven fiberglass cloth laminate with an epoxy resin binder, such as FR-4.

In some embodiments of a ribbon-connection, the density of the bonding sites for an area on the printed wiring board is greater than the density of bonding sites for the same area on a printed wiring board that uses one or more bond pads. In some embodiments, the profile of the ribbon welded to the printed wiring board and the electrical component may be lower than the profile obtained when the ribbon is welded to the printed wiring board and the electrical component using one or more bond pads.

The present ribbon-connections may include a printed wiring board for use in an implantable medical device, such as a circuit board connected via ribbon comprising titanium to an electrical component, such as a radiofrequency module, electrical lead, or battery terminal.

DRAWINGS

The present technology will become more fully understood from the detailed description and the accompanying drawings.

FIG. 1 illustrates side-views of a prior art ribbon-connection in panel (a) and an embodiment of a ribbon-connection constructed according to the present disclosure in panel (b); and FIG. 2 illustrates top-views of a prior art ribbon-connection in panel (a) and an embodiment of a ribbon-connection constructed according to the present disclosure in panel (b).

It should be noted that the figures set forth herein are intended to exemplify the general characteristics of apparatus, systems, and methods among those of the present technology, for the purpose of the description of specific embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to electrical coupling of electronic components. For example, a printed wiring board (PWB) may be directly interconnected to one or more electrical components. These electrical connections are made by conductively coupling two electrical components using a ribbon comprising titanium that is directly attached to each component without the use of bond pads or bond pad arrays, for example, by laser welding the ribbon.

In some embodiments, a ribbon-connection comprises a printed wiring board including a first bonding site, an electrical component including a second bonding site, and a ribbon comprising titanium. The ribbon has a first end welded to the first bonding site of the printed wiring board and a second end welded to the second bonding site of the electrical component. The weld at the first bonding site directly contacts the printed wiring board, where there is no bond pad between the ribbon and the first bonding site. In a similar fashion, the weld at the second bonding site may directly contact the electrical component, with no bond pad between the ribbon and the second bonding site.

In some embodiments, an electrical component and/or a PWB is ribbon bonded directly using ribbon comprising titanium, where the ribbon is not attached or welded using a block, bond pad, or bond pad array (BPA) on the electrical component. In some cases, the ribbon is essentially pure titanium, such as grade 2 titanium. For example, the ribbon may consist essentially of titanium and may also consist solely of titanium. The ribbon may have a substantially rectangular cross-section of about 0.005 inches wide and about 0.0005 inches thick. In some embodiments, the ribbon may ribbon may be as wide as about 0.015 inches and as thick as about 0.002 inches. Other ribbon cross-sections are possible, such as oval or square, and in some embodiments the ribbon may have a substantially circular cross-section. For example, where the ribbon has a substantially circular cross-section, it may be in the form of wire comprising titanium. Ribbon having a substantially rectangular cross-section is generally preferred over ribbon having a substantially circular cross-section, generally known as wire.

In addition, suitable ribbons can include the following aspects. Titanium ribbons of grades 5 or 9 may used. A suitable ribbon supplier is Fort Wayne Metals located in Fort Wayne, Ind. In some embodiments, nickel plated copper ribbon may be used in place of the ribbon comprising titanium. The nickel plated copper ribbon may have the various shapes, forms, and dimensions as the ribbon comprising titanium.

While not being bound by theory, it is believed that metallurgical aspects of titanium bonded to nickel/niobium are particularly useful in the present technology. Titanium bonding to nickel and/or niobium allows the metals to mix very well in the intermetallic zone and the resultant bonds are not brittle, the bonds being resistant to the effects of vibration and temperature. What is more, the ribbon comprising titanium (versus other metals) can bond to the nickel layer of a PWB and not affect underlying metal layers, such as a copper layer. The titanium is easily combined with the nickel layer due to the fact that the melting point of nickel is slightly lower than titanium, so when the melting point of titanium is reached (where most of the gold boils off, although some gold may remain in the intermetallic layer) the nickel melts into the titanium, and the copper layer below is not detrimentally affected due to the fact that it conducts away the heat so rapidly. Surprisingly and unexpectedly the ribbon comprising titanium (versus other metals and/or connectors, such as gold or aluminum) is attached to the nickel layer and does not detrimentally affect an underlying copper layer.

The present technology allows the manufacture of ribbon-connections where the ribbon bond formed between the ribbon and a metal layer (e.g., nickel) of the PWB or electrical component does not affecting other metal layers (e.g., copper) or the substrate (e.g., Nelco substrate, for example, as available from Park Electrochemical Corporation in Melville, N.Y.) of the PWB or electrical component. For example, when using laser welding to attach the ribbon, about 0.013 joules of energy may be applied to form a welding spot having an average diameter of about 0.002 inches, thereby minimizing or eliminating damage caused by overheating the electronic component and/or PWB. In some cases, the weld at the bonding site may have an average diameter ranging from about 0.001 inches to about 0.003 inches.

By using ribbon comprising titanium and laser welding, ribbon bonds can be made directly to the PWB. This eliminates the need for bond pads, such as gold blocks, and/or bond pad arrays, and consequently reduces the space necessary for bonds, minimizes the spacing between bonds, and eliminates the spacing needed between bond pads or BPAs and other components. In addition, the profile and height required for ribbon bonding between electrical components may also be reduced as any elevation provided by the bond pad or BPA is absent. Fabrication of electronic devices is simplified, component and labor costs are reduced, and time savings are realized.

In some embodiments, the ribbon-connection includes a printed wiring board that further comprises a second electrically conductive layer, wherein at least a portion of the second electrically conductive layer is located along the first electrically conductive layer opposite of the first bond site. For example, the first and second electrically conductive layers may be in the form of parallel planes, with the first bond site on one side of the first electrically conductive layer and the second electrically conductive layer disposed on the other side of the first electrically conductive layer. The second electrically conductive layer may comprise copper and the printed wiring board may further comprise a woven fiberglass cloth laminate with an epoxy resin binder. For example, the woven glass cloth laminate with an epoxy resin binder may be FR-4. Suitable PWBs and substrates for PWBs include those from Hitachi (Tokyo, Japan) and Multek (Northfield, Minn.).

In some embodiments, the weld at the first bond site does not affect the second electrically conductive layer. For example, when the first end of the ribbon is welded to the first bonding site, contacting the first electrically conductive layer, the welding process does not substantially affect the integrity or material properties of the underlying second electrically conductive layer. The portion of the second electrically conductive layer located along the first electrically conductive layer opposite of the first bond site may be substantially similar to another portion of the second electrically conductive layer not opposite of the first bond site.

The present ribbon-connections can be used in a wide variety of implantable medical devices (IMDs) that employ electronic circuitry for providing electrical stimulation of body tissue and/or monitoring a physiologic condition. For example, the printed wiring board of the ribbon-connection may be a circuit board for an implantable medical device. In some cases, the electrical component of the ribbon-connection can be another printed wiring board; i.e., two (or more) PWBs may be joined by ribbon bonds. One or more electrical components may also be connected to each other or to one or more PWBs with ribbon by laser welding. Examples of IMDs include implantable pulse generators (IPG), cardiac pacemakers, pacemaker-cardioverter-defibrillators, nerve, muscle and neurological stimulators, cardiomyostimulators, implantable drug dispensers, implantable cardiac signal monitors and recorders, and the like. IMDs may include PWBs and electrical components such as an integrated circuit, charging capacitor, battery or battery terminal, radiofrequency module, electrical lead and other components that are enclosed in hermetically sealed metallic housings. The various PWBs and electrical components of an IMD may each be interconnected via ribbon comprising titanium using laser welding, allowing the various bonding sites on the PWB(s) and electrical component(s) to forgo the use of bonding pads or bond pad arrays. Such bonding sites may comprise a conductive metal, such as nickel or niobium, to which the ribbon is welded.

In some cases, IMDs are capable of two-way communication or telemetry between the IMD and an external device; e.g., a programmer. For example, where the IMD is a pacemaker system, a programmer can download data to the implanted pacemaker, such as operating instructions and software. Likewise, data may flow in the opposite direction, that is, from the implanted pacemaker to the programmer for analysis. In fact, modern pacemakers are capable of storing significant amounts of data about the patient (e.g., average heart rate) and the pacemaker itself (e.g., battery status), which may need to be frequently transmitted to the programmer for evaluation by the physician.

One way of communicating with an IMD, for example, is through radiofrequency (RF) telemetry transmission, which relies upon magnetic field coupling through the patient's skin of an IMD antenna with a closely spaced programmer antenna. An RF telemetry antenna is positioned outside the hermetically sealed IMD housing, which allows it to operate in a high frequency RF telemetry bandwidth and reduces space requirements inside the housing. The RF telemetry antenna is connected to an antenna feedthrough. An RF telemetry module is connected to the antenna feedthrough and the RF telemetry antenna within the hermetically sealed IMD housing. The RF telemetry module is also connected to an IMD circuit board, such as a PWB. For example, the present technology may laser weld titanium ribbon to connect an RF module and a circuit board inside an IMD housing. The present ribbon bonding methods can also accommodate automated assembly of the two (or more) components to form various ribbon-connections.

It will be appreciated by those skilled in the art, however, that the present technology may be used in various microelectronic applications. These include, but are not limited to, semiconductor production and microchip utilization, integrated circuit packaging and mounting, and other electrical interconnections in the computer hardware and electronics industries. For example, the ribbon comprising titanium may be bonded directly to sputtered Ti45Nb on silica and silicone wafers.

Referring now to FIG. 1, a side view of a prior art ribbon-connection 100 is shown in panel (a). One end of a metallic ribbon 105, for example an aluminum or gold ribbon, is bonded to a bond pad 110 affixed to a printed wiring board 115, which uses a Nelco substrate, for example. The printed wiring board 115 has a gold layer 117, nickel layer 120, copper layer 125, and a support layer 130 of woven fiberglass cloth with epoxy resin binder. The gold layer 117 helps prevent the nickel layer 120 from oxidizing during storage. The other end of the metallic ribbon 105 is bonded to an electrical component 135. The ribbon-connection profile 140 corresponds to the height of the metallic ribbon 105 between the bond to the bond pad 110 affixed to the printed wiring board 115 and the bond to the electrical component 135. Changes in elevation or position between the printed wiring board 115 and the electrical component 135 affect the profile 140, but in all cases the profile 140 is affected in part by the size of the bond pad 110 affixed to the printed wiring board 115.

Panel (b) of FIG. 1 shows a side view of a ribbon-connection 145 constructed according to the present technology. A ribbon comprising titanium 150 is directly bonded at one end to the printed wiring board's 155 nickel layer 160. During bonding, heat can melt away an oxidation protecting gold layer 157, so that the ribbon directly contacts and is bonded to the nickel layer 155. The copper layer 165 underlying the nickel layer 160 at the bond site is unaffected by heat and/or force used in the bonding process. A support layer 170 of woven fiberglass cloth with epoxy resin binder underlies the copper layer 165. The other end of the ribbon comprising titanium 150 is bonded to an electrical component 175. The ribbon-connection profile 180 of the present technology corresponds to the height of the ribbon comprising titanium 150 between the bond to the nickel layer 160 of the printed wiring board 155 and the bond to the electrical component 175. Changes in elevation or position between the printed wiring board 155 and the electrical component 175 can affect the profile 180, but there is no contribution to the profile provided by a bond pad. For example, where printed wiring boards 115, 155 and electronic components 135, 175 have identical spatial relations, the profile 140 of the prior art ribbon connection 100 is greater than the profile 180 of the present ribbon-connection 145 due to contribution of the bond pad 110 and the need to provide looping of the ribbons 105, 150 during the bonding process. For example, smaller ribbon-connections are possible, where the ribbon-connection is reduced in at least one or more dimensions.

Referring now to FIG. 2, panel (a) shows a top view of a ribbon-connection 200 having a plurality of metallic ribbons, as found in the prior art. In this case, five ribbon-connections are illustrated that include a printed wiring board 205 and metallic ribbons 210 that are bonded to bond pads 215 affixed to the printed wiring board 205. The other ends of the metallic ribbons 210 are bonded to one or more electrical components or other printed wiring boards (not shown). For a given area of the printed wiring board 220, defined by the distance illustrated by 220, the density of metallic ribbons 210 that can be connected to the printed wiring board is affected by the size and spacing of the bond pads 215, where the bond pads 215 are larger than the footprints of the bonded metallic ribbons 210.

Panel (b) of FIG. 2 shows a top view of a ribbon-connection 225 having a plurality of ribbons comprising titanium constructed according to the present technology. As shown, a printed wiring board 230 is directly connected to eight ribbons comprising titanium 235 without the use of bond pads. The other ends of the ribbons comprising titanium 235 are bonded to one or more electrical components or other printed wiring boards (not shown). For a given area of the printed wiring board 230, defined by the distance illustrated by 240, the density of the ribbons 235 that can be connected to the printed wiring board is affected by the size and spacing of the footprints of the bonded ribbons 235, and is not constrained by size and spacing requirements of bond pads. For equivalent distances, such as where 220 and 240 are equal, the density of ribbons 235 of the present ribbon-connection 225 can be greater than the density of ribbons 210 of the prior art ribbon-connection 200. In the examples shown in FIG. 2, panels (a) and (b), the present technology allows eight ribbons to fit in the same space as five ribbons that use bond pads. However, the present technology may have about twice as many ribbons for a given area as connections that employ blocks, bond pads, or bond pad arrays; e.g., about 20 ribbons in the present ribbon-connection versus about 10 ribbons in a ribbon-connection employing bond pads. In some cases, there may be up to about four times as many ribbons for a given area as compared to connections employing bond pads.

The present ribbon-connections may be manufactured using the laser welding apparatuses and methods as described by U.S. Pat. Nos. 6,501,043 (issued Dec. 31, 2002) and U.S. Pat. No. 6,717,100 (issued Apr. 6, 2004) both to Ruben; collectively referred to herein as Ruben, and assigned to the assignee of the present invention, the disclosure of which is incorporated by reference in its entirety herein. The present ribbon comprising titanium is used in place of the metal ribbons described in Ruben and the ribbon comprising titanium is bonded directly to one or more electrical components and/or printed wiring boards without the use of a bond pad, bond pad array, or block. For example, the ribbon comprising titanium is welded directly to a first bond site and a second bond site using an apparatus having a bond head and a laser beam in order to form a connection loop, where the first and/or second bond sites do not include a bond pad, bond pad array, or block.

As described and illustrated by Ruben, a representative bonding apparatus includes a portion described as a bond head. The ribbon can be supplied on a standard spool and the bond head can be adapted to receive the ribbon through a threading slot. The threading slot has a ribbon entrance and ribbon exit and the slot allow use of ribbons of various thicknesses. From the threading slot, the ribbon is disposed under the bond foot and may be welded to the bond substrate by a laser beam, where the bond substrate is a printed wiring board or electronic component, for example.

As described by Ruben, in some embodiments the laser is not directed by optic fiber to the bond site through the bond head. In such cases, the bond head may be adapted to have a laser aperture to admit laser light that portion of ribbon disposed over bond site. The ribbon may initially be threaded through the threading slot in the bond head, to ensure proper placement of the ribbon relative to the bond head. As described therein, the bond head descends to the bond surface and forces the ribbon to contact the substrate to be bonded; e.g., PWB or electronic component. Once the predetermined load is applied, a laser may be fired in order to weld the ribbon comprising titanium to bond site.

Manufacture of the present ribbon-connections may employ the Ruben processes of connection loop formation, as depicted in Ruben. The present ribbon-connections may also employ the bonding variations as provided by Ruben, including "security welds;" i.e., double or other multiple welds may be effected at each bond site. These security welds serve to increase contact area for improved current flow, mechanical strength, and reliability. The bonder makes the weld, moves slightly and welds the ribbon again to the same terminal. The welds may overlap, may combine to form a single uniform weld nugget, or may be completely separate effecting discrete weld nuggets. Manufacture of the present ribbon-connections may also be performed using the Ruben apparatuses and methods in fully automatic, semi-automatic, or manual modes, as described therein.

Lasers as described by Ruben may be used to weld the ribbon comprising titanium to the bonding sites on the printed wiring board and/or the electrical component. For example, a Nd:YAG 355-1,064 nm laser may be used. Generally, however, the laser source to effect the bonding may be a high power pulsed or continuous wave (CW) laser; e.g., NdYAG, Ar-ion, Carbon dioxide, or Cu vapor. A suitable laser is a Nd:YAG Pulsed Laser output of about 1 joule/pulse, with a pulse width of about 1-5 msec, and a pulse strength of about 1000-2000 watts. The power required to generate the required heat is thought typically to be about 1-10 watts or more of average power; e.g., providing a 1 msec, 1000 watt pulse every second would be equivalent to about 1 watt of CW operation. Because of the localized heat imparted by laser beam, damage to underlying and adjacent materials is avoided. For example, when the ribbon comprising titanium is laser-welded to a bond site on the PWB, a direct bond may be formed with the nickel layer of the PWB without substantially affecting the underlying copper layer and Nelco substrate. The materials to be laser welded adsorb sufficient light from the laser such that their heat is increased above solidus. Certain highly reflective materials may not absorb sufficient laser light to effect sufficient heat rise. The present ribbon comprising titanium and the bonding sites comprising titanium and/or niobium absorb enough light for laser welding.

The present technology provides the (1) ability to ribbon bond directly to a printed wiring board; (2) eliminates the need for blocks, bond pads, or bond pad arrays and simplifies manufacturing; (3) reduces spacing between bonds; (4) eliminates the spacing needed for blocks and BPAs; (5) reduces the height required for blocks/BPAs and wire bonding; (6) reduces component cost; (7) saves manufacturing time; and (7) reduces labor costs.

As described, the present technology may include and/or modify the apparatuses and methods in U.S. Pat. Nos. 6,717,100 and 6,501,043, both to Ruben. The present technology may further employ the methods and apparatuses for automated assembly and laser welding of medical devices as described U.S. Pub. No. 2005/0284919 to Boyd and WO2006/015068. The present technology may also be used for microelectronic bonding in the implantable medical device art, for example, as illustrated in U.S. Pat. No. 5,535,097 to Ruben, et al. and U.S. Pat. No. 5,522,861 to Sikorski, et al. By way of example, the present technology may be used to make electrical connectors between and among the hybrid circuit, battery, capacitors, feedthroughs, and other components of implantable medical devices.

The embodiments described herein are exemplary and not intended to be limiting in describing the full scope of compositions and methods of the present technology. Equivalent changes, modifications and variations of embodiments, materials, compositions and methods can be made within the scope of the present technology, with substantially similar results.

What is claimed is:

1. A ribbon-connection for a circuit in an implantable medical device comprising:
   a printed wiring board comprising at least a support layer, a second electrically conductive layer supported by the support layer, and one or more first electrically conductive layers provided along the second electrically conductive layer, wherein the one or more first electrically conductive layers provided along the second electrically conductive layer provide at least a first bonding site and wherein the one or more first electrically conductive layers comprise nickel or niobium;
   an electrical component comprising one or more second bonding sites to be electrically connected to the printed wiring board; and
   a ribbon comprising titanium, wherein the ribbon comprises a substantially rectangular cross-section, and further wherein the ribbon comprises a first end laser welded to the first bonding site of the one or more first electrically conductive layers and a second end welded to a bonding site of the one or more second bonding sites of the electrical component, wherein the first end of the ribbon directly contacts the bonding site of the one or more first electrically conductive layers of the printed wiring board.

2. The ribbon-connection of claim 1, wherein the second end of the ribbon directly contacts the bonding site of the one or more bonding sites of the electrical component.

3. The ribbon-connection of claim 1 wherein at least a portion of the second electrically conductive layer is located along and in contact with the one or more first electrically conductive layers opposite of the first bonding site.

4. The ribbon-connection of claim 1, wherein the melting points of the one or more first electrically conductive layers and the second conductive layer are such that, during laser welding of the ribbon to the first bonding site, at least a portion of the first bonding site of the one or more first electrically conductive layers melts with the first end of the ribbon that directly contacts the bonding site to form an electrical connection as a result of the weld at the first bonding site, wherein the second electrically conductive layer conducts away heat resulting from the weld.

5. The ribbon-connection of claim 1, wherein the second electrically conductive layer and the one or more first electrically conductive layers are parallel.

6. The ribbon-connection of claim 1, wherein the second electrically conductive layer comprises copper.

7. The ribbon-connection of claim 1, wherein the printed wiring board comprises a woven fiberglass cloth laminate with an epoxy resin binder.

8. The ribbon-connection of claim 7, wherein the woven glass cloth laminate with an epoxy resin binder is FR-4.

9. The ribbon-connection of claim 1, wherein the second end of the ribbon directly contacts the bonding site of the electrical component which comprises a conductive metal.

10. The ribbon-connection of claim 9, wherein the conductive metal comprises at least one of titanium, nickel, and niobium.

11. The ribbon-connection of claim 1, wherein the ribbon has a substantially rectangular cross-section of about 0.005" wide and about 0.0005" thick.

12. The ribbon-connection of claim 1, wherein the weld at the first bonding site of the one or more first electrically conductive layers comprises an area having about a 0.002" average diameter.

13. The ribbon-connection of claim 1, wherein the printed wiring board further comprises a plurality of first bonding sites, and the ribbon-connection further comprises a plurality of ribbons comprising titanium, where each ribbon includes a first end welded to one of the first bonding sites of the printed wiring board and a second end welded to a bonding site of the one or more second bonding sites on the electrical component or on another electrical component.

14. The ribbon-connection of claim 1, wherein the printed wiring board comprises an implantable medical device circuit board.

15. The ribbon-connection of claim 1, wherein the electrical component comprises a radiofrequency module, electrical lead, or battery terminal.

16. A ribbon-connection for a circuit in an implantable medical device comprising:
    a printed wiring board comprising at least one or more electrically conductive layers, the one or more electrically conductive layers comprising a nickel layer;
    an electrical component comprising a bonding site; and
    a ribbon comprising titanium, wherein the ribbon comprises a substantially rectangular cross-section, and further wherein the ribbon comprises a first end where titanium is laser welded directly to the nickel layer of the printed wiring board and a second end welded to the bonding site of the electrical component.

17. A method of forming a ribbon-connection for a circuit in an implantable medical device comprising:
    providing a printed wiring board comprising at least a support layer, a second electrically conductive layer supported by the support layer, and one or more first electrically conductive layers provided along the second electrically conductive layer, wherein the one or more first electrically conductive layers provided along the second electrically conductive layer provide at least a first bonding site, and wherein one or more first electrically conductive layers comprise nickel or niobium;
    providing an electrical component comprising one or more second bonding sites to be electrically connected to the printed wiring board;
    providing a ribbon comprising titanium, wherein the ribbon comprises a substantially rectangular cross-section extending from a first end to a second end;
    laser welding the first end of the ribbon comprising titanium directly to the first bonding site; and
    welding the second end of the ribbon directly to a bonding site of the one or more second bonding sites of the electrical component.

18. A method of forming a ribbon-connection for a circuit in an implantable medical device comprising:
    providing a printed wiring board comprising at least one or more electrically conductive layers, the one or more electrically conductive layers comprising a nickel layer;
    providing an electrical component comprising one or more bonding sites to be electrically connected to the printed wiring board;
    providing a ribbon comprising titanium, wherein the ribbon comprises a substantially rectangular cross-section;
    connecting a first end of the ribbon directly to the nickel layer of the printed wiring board via laser welding; and
    connecting a second end of the ribbon directly to a bonding site of the one or more bonding sites of the electrical component.

19. A ribbon-connection for a circuit in an implantable medical device comprising:
    a printed wiring board comprising at least a support layer, a second electrically conductive layer supported by the support layer, and one or more first electrically conductive layers provided along the second electrically conductive layer,
        wherein the one or more first electrically conductive layers provided along the second electrically conductive layer provide at least a first bonding site,
        wherein the one or more first electrically conductive layers comprise nickel or niobium,
        wherein the first and second electrically conductive layers are disposed in parallel planes with the first bond site is on one side of the first electrically conductive layer and the second electrically conductive layer is on the other side of the first electrically conductive layer, and
        wherein the first conductive layer is exposed at a surface of the printed wiring board;
    an electrical component comprising one or more second bonding sites to be electrically connected to the printed wiring board; and
    a ribbon comprising titanium,
        wherein the ribbon comprises a substantially rectangular cross-section,
        wherein the ribbon comprises a first end laser welded to the first bonding site of the one or more first electrically conductive layers and a second end welded to a bonding site of the one or more second bonding sites of the electrical component, and
        wherein the first end of the ribbon directly contacts the bonding site of the one or more first electrically conductive layers of the printed wiring board.

20. The ribbon-connection of claim 19, wherein second electrically conductive layer comprises copper.

21. The ribbon-connection of claim 19, wherein the first and second electrically conductive layers form a trace within the printed wiring board.

* * * * *